United States Patent
Kwon

(10) Patent No.: US 9,395,330 B2
(45) Date of Patent: Jul. 19, 2016

(54) DEGRADABLE POLYACRYLAMIDE GEL

(75) Inventor: Young Jik Kwon, Irvine, CA (US)

(73) Assignee: Case Western Reserve University, Cleveland, OH (US)

(*) Notice: Subject to any disclaimer, the term of this patent is extended or adjusted under 35 U.S.C. 154(b) by 1553 days.

(21) Appl. No.: 12/051,680

(22) Filed: Mar. 19, 2008

(65) Prior Publication Data

US 2009/0145758 A1 Jun. 11, 2009

Related U.S. Application Data

(60) Provisional application No. 60/895,556, filed on Mar. 19, 2007.

(51) Int. Cl.
*G01N 27/447* (2006.01)

(52) U.S. Cl.
CPC .................. *G01N 27/44747* (2013.01)

(58) Field of Classification Search
CPC .................. G01N 27/447–27/44795
USPC ................ 204/456, 462, 466, 606, 613, 616
See application file for complete search history.

(56) References Cited

U.S. PATENT DOCUMENTS

| | | | | |
|---|---|---|---|---|
| 4,151,065 A | * | 4/1979 | Kaplan et al. | 204/620 |
| 5,225,062 A | * | 7/1993 | Yoshioka et al. | 204/469 |

OTHER PUBLICATIONS

Kwon, Y. J., et al., "Directed Antigen Presentation Using Polymeric Microparticulate Carriers Degradable at Lysosomal pH for Controlled Immune Responses", Molecular Pharmaceutics, vol. 2, No. 1, Feb. 2005, p. 83-91.*

Alpers, David H., "Method for Determination of Specific Activity of Proteins in Polyacrylamide Gels", Analytical Biochemistry 35, 314-320 (1970).

Galvani, Marina, et al., "Investigating the Reaction of a Number of Gel electrophoresis cross-linkers with β-lactoglobulin by Matrix assisted laser desorption/ionization mass spectrometry" Electrophoresis 2000, 21, 3684-3692.

Krause, Frank, et al., "Preparation isolation of protein complexes and other bioparticles by elution from polyacrylamide gels", Electrophoresis 2008, 29, 2617-2636.

O'Connell, P.B.H., et al., "Polyacrylamide Gels with Modified Cross-Linkages", Analytical Biochemistry 76, 63-73 (1976).

Seymour, Jana L. et al., "Native Gel Activity Stain and Preparation Electrophoretic Method for the Detection and Purification of Pyridine Nucleotide-Linked Dehydrongenases", Analytical Biochemistry 178, 243-247 (1989).

Spath, P.J., et al., "Properties of SDS-Polyacrylamide Gels Highly Cross-Linked with N,N'-diallyltartardiamide and the Rapid Isolation of Macromolecules from the Gel Matrix", Analytical Biochemistry 93, 275-285 (1979).

* cited by examiner

*Primary Examiner* — J. Christopher Ball
(74) *Attorney, Agent, or Firm* — Tarolli, Sundheim, Covell & Tummino LLP

(57) ABSTRACT

A degradable polyacrylamide gel for analyzing or separating at least one macromolecule in a sample using electrophoresis includes a polyacrylamide cross-linked with at least one degradable cross-linker having a ketal or acetal group with the formula (I), wherein $R_1$ and $R_2$ are the same or different and are hydrogen, an alkyl, or a substituted alkyl.

17 Claims, 15 Drawing Sheets

DEGRADABLE POLYACRYLAMIDE GEL

RELATED APPLICATION

This application claims priority from U.S. Provisional Application No. 60/895,556 filed Mar. 19, 2007, the subject matter, which is incorporated herein by reference.

TECHNICAL FIELD

The present invention generally relates to gel electrophoresis, and more particularly to a degradable polyacrylamide gel for separating or analyzing at least one macromolecule in a sample.

BACKGROUND OF THE INVENTION

In the field of analyzing macromolecules, one-dimensional and two-dimensional gel electrophoresis have become standard tools for separating and visualizing macromolecules. One-dimensional gel electrophoresis is used to separate mixtures of macromolecules, such as proteins, into individual components according to differences in mass by electrophoresing in a polyacrylamide gel under denaturing conditions.

Two-dimensional gel electrophoresis involves isoelectric focusing to separate proteins electrophoretically on the basis of their relative acidic and basic residue content. Under the influence of an applied electric field, a more highly charged protein will move faster than a less highly charged protein of similar size and shape. If the proteins are made to move from a sample zone through a non-convecting medium (e.g., polyacrylamide), an electrophoretic separation will result. When the protein enters a region that has a pH value at which the protein's net charge is zero (the isoelectric point), it will cease to migrate relative to the medium. Further, if the migration occurs through a pH gradient that increases monotonically from the anode, the protein will "focus" at its isoelectric point.

Polyacrylamide gels comprising polyacrylamide cross-linked by bis-acrylamide are primarily the medium of choice for protein analysis. Currently available gels are non-dissolvable and repeatedly show retention of proteins after transfer to the second dimension. Compounding this problem, once resolved onto the second dimension, further protein retention and losses occur with preceding manipulations. Although yields approach 80-90% recovery using traditional methods (i.e., mechanical, electro-elution, and diffusion methods), total recovery is rarely achieved. Further, chemical disruption of the gel matrix band often modifies the protein, in turn altering its native characteristics and having a negative impact on later protein identification. In each step of conventional polyacrylamide gel assays, information is inevitably lost through protein retention in the gel.

SUMMARY OF THE INVENTION

The present invention relates to a degradable polyacrylamide gel for separating or analyzing at least one macromolecule in a sample. According to one aspect of the present invention, the degradable polyacrylamide gel comprises a polyacrylamide that is cross-linked with at least one degradable cross-linker having a ketal or acetal group with the formula (I):

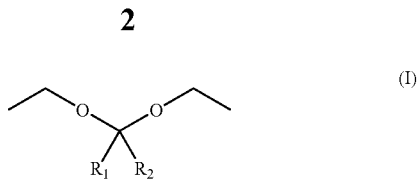

wherein $R_1$ and $R_2$ are the same or different and are hydrogen, an alkyl, or a substituted alkyl.

In another aspect of the present invention, a degradable polyacrylamide gel for analyzing or separating at least one macromolecule in a sample using electrophoresis comprises a polyacrylamide that is cross-linked with at least one degradable cross-linker including a ketal or acetal group having the formula (II):

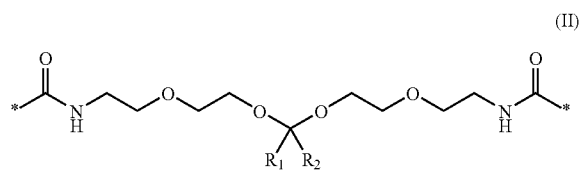

wherein $R_1$ and $R_2$ are the same or different and are hydrogen, an alkyl, or a substituted alkyl.

In another aspect of the present invention, a method is provided for preparing a degradable polyacrylamide gel. The method comprises the step of cross-linking an acrylamide polymer with at least one degradable cross-linker including the formula (III):

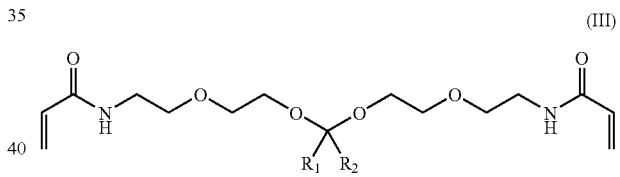

wherein $R_1$ and $R_2$ are the same or different and are hydrogen, an alkyl, or a substituted alkyl.

In another aspect of the present invention, a method is provided for separating or analyzing at least one macromolecule in a sample. One step of the method includes providing a degradable polyacrylamide gel comprising a polyacrylamide that is cross-linked with at least one degradable cross-linker including a ketal or acetal group having the formula (I):

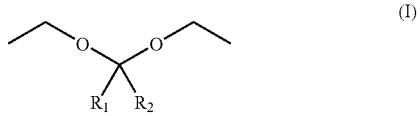

wherein $R_1$ and $R_2$ are the same or different and are hydrogen, an alkyl, or a substituted alkyl. At least one sample is loaded into the degradable polyacrylamide gel. Electrophoresis is then performed on the degradable polyacrylamide gel, and the gel is stained to visualize the at least macromolecule contained therein.

In another aspect of the present invention, a method is provided for separating or analyzing at least one macromolecule in a sample. One step of the method includes providing a degradable polyacrylamide gel comprising a polyacrylamide cross-linked with at least one degradable cross-linker including a ketal or acetal group having the formula (I):

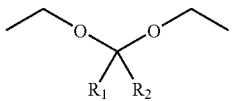

wherein $R_1$ and $R_2$ are the same or different and are hydrogen, an alkyl, or a substituted alkyl. Next, the at least one sample is loaded into the degradable polyacrylamide gel. Electrophoresis is then performed on the degradable polyacrylamide gel, and the gel is stained to visualize the at least macromolecule contained therein. At least one fraction containing the at least one macromolecule is excised from the degradable polyacrylamide gel and at least partially solubilized.

In another aspect of the present invention, an electrophoresis apparatus for separating or analyzing at least one macromolecule in a sample is provided. The electrophoretic apparatus comprises an electrophoretic cell and a degradable polyacrylamide gel disposed in the electrophoretic cell. The degradable polyacrylamide gel comprises polyacrylamide that is cross-linked with at least one degradable cross-linker including a ketal or acetal group having the formula (I):

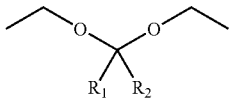

wherein $R_1$ and $R_2$ are the same or different and are hydrogen, an alkyl, or a substituted alkyl. The electrophoretic cell comprises a tank, an upper tank, and a cover set for the tank. The upper tank is disposable inside the tank and capable of receiving a cassette which houses the degradable polyacrylamide gel. The cover set and the tank each respectively include a cathode and an anode for conducting an electric current therebetween. The electrophoretic cell is operably coupled to a power source.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 5A is a degradable polyacrylamide gel containing protein marker and BSA. FIG. 5B is a confirmation of purified intact proteins using a conventional polyacrylamide gel (FIG. 5A);

FIG. 6A shows the degradable polyacrylamide gel of FIG. 5A FIG. 6B shows a bicinchoninic acid (BCA) analysis of the recovered BSA proteins.

DETAILED DESCRIPTION

Figure 1:
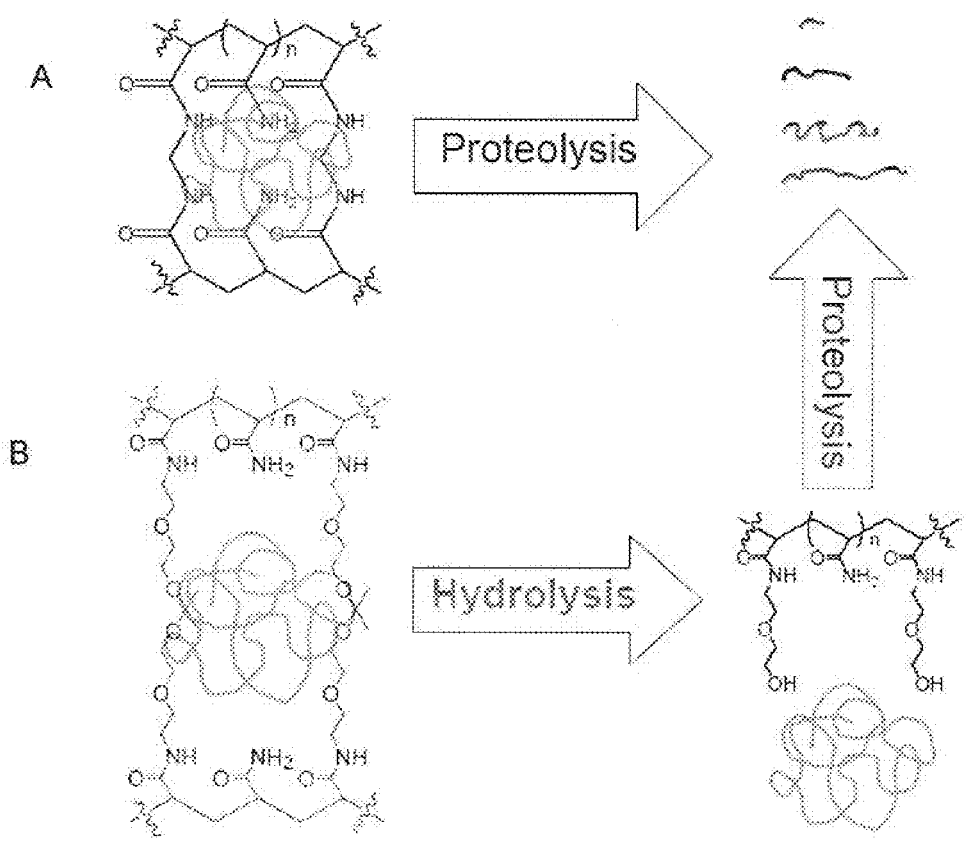
FIGS. 1A-B are a schematic representation comparing polyacrylamide gel structure and function of the prior art (FIG. 1A) and the present invention (FIG. 1B)

The present invention generally relates to gel electrophoresis, and more particularly to a degradable polyacrylamide gel for separating or analyzing at least one macromolecule in a sample. The present invention is based on the discovery that a polyacrylamide can be cross-linked with a degradable cross-linker to form a degradable polyacrylamide gel. The present invention is also based on the discovery that the degradable polyacrylamide gel allows highly efficient isolation and recovery of structurally intact macromolecules, such as proteins. Based on this discovery, the present invention provides a degradable polyacrylamide gel, a method for making the degradable polyacrylamide gel, a method for analyzing or separating macromolecules using the degradable polyacrylamide gel, and an electrophoresis apparatus for analyzing or separating macromolecules.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "ketal" refers to a functional group bearing two alkyl groups and two alkoxy groups on one carbon atom. Ketals typically have the formula $R_2C(OR)_2$ and are produced in the acid-catalyzed alcoholysis of a ketone or a hemiketal.

As used herein, the term "acetyl" refers to a functional group bearing an alkyl group, a hydrogen atom, and two alkoxy groups on one carbon atom. Acetals typically have the formula RCH(OR)₂ and are produced in the acid-catalyzed alcoholysis of an aldehyde or a hemiacetal.

As used herein, the terms "alkyl" or "substituted alkyl" refer to a straight chain or branched chain hydrocarbon radical having from about 1 to about 10 carbon atoms. Examples of such alkyls or substituted alkyls include methyl, ethyl, n-propyl, isopropyl, n-butyl, isobutyl, s-butyl, t-butyl, pentyl, neopentyl, hexyl, isohexyl, and the like.

As used herein, the term "macromolecule" refers to any molecule having a molecular weight from the hundreds up to the millions. Macromolecules can include polypeptides, proteins, polynucleotides, nucleic acids, polysaccharides, carbohydrates, and other such molecules that are generally synthesized by biological organisms, but can be prepared synthetically or using recombinant molecular biology methods.

As used herein, the term "electrophoresis" refers to the movement of charged macromolecules suspended in a separation medium (e.g., polyacrylamide or agarose) under the influence of an applied electric field. If the electric field is applied between electrodes in a cell, the macromolecules may migrate, depending on their polarity, to either a cathode or anode while the separation medium remains substantially stationary. When a coincident voltage is applied to the electrodes, the macromolecules in the separation medium may migrate under the influence of the electric field to the anode or cathode having a polarity opposite from their own.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term also encompasses nucleic acids, i.e., oligonucleotides, containing known analogues of natural nucleotides. The term also encompasses nucleic acid-like structures with synthetic backbones.

As used herein, the term "polypeptide" refers to an oligopeptide, peptide, polypeptide, or protein sequence, or to a fragment, portion, or subunit of any of these, and to naturally occurring or synthetic molecules. The terms "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

In one aspect of the present invention, the degradable polyacrylamide gel may comprise a polyacrylamide that is cross-linked with at least one degradable cross-linker. The at least one degradable cross-linker can include a ketal or acetal group, and may comprise the formula (I):

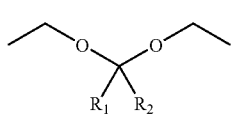

(I)

wherein $R_1$ and $R_2$ may be the same or different, and may include hydrogen, an alkyl, or a substituted alkyl.

Alternatively or additionally, the at least one degradable cross-linker may comprise a ketal or acetal group having the formula (II):

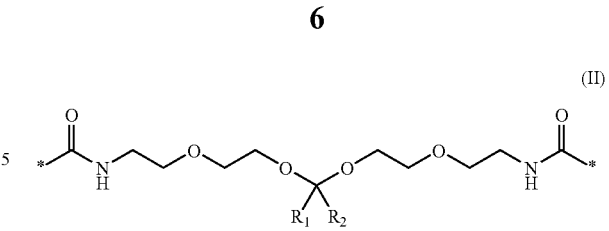

(II)

wherein $R_1$ and $R_2$ are the same or different and are hydrogen, an alkyl, or a substituted alkyl.

The polyacrylamide is formed from an acrylamide monomer, also known as acryl amide and 2-propenamide, having the chemical formula $C_3H_5NO$. As described in further detail below, at least one catalyst and at least one initiator may be used to initiate polymerization of the acrylamide monomer and the at least one degradable cross-linker. For instance, tetramethylethylenediamine (TEMED or TMEDA) may be used with ammonium persulfate to catalyze the formation of the degradable polyacrylamide gel.

Degradable polyacrylamide gels of the present invention can be used for any type of gel electrophoresis to separate and isolate macromolecules. For example, degradable polyacrylamide gels can be used to form slab gels, such as those used in horizontal electrophoresis, or used in capillary electrophoresis. Alternatively, degradable polyacrylamide gels can be configured for use in high-throughput protein separations. Electrophoresis techniques are well known in the art and can be readily adapted by one of ordinary skill in the art for use with the degradable polyacrylamide gels of the present invention.

The ketal or acetal groups of the degradable polyacrylamide gels of the present invention can be readily hydrolyzed after separation and/or isolation of the macromolecules. Hydrolysis of the degradable cross-linker allows release of structurally intact macromolecules from the polyacrylamide matrix (FIG. 1B) in contrast to conventional polyacrylamide gels that prevent or hinder release of intact proteins upon degradation of the polyacrylamide gel (FIG. 1A). The degradable polyacrylamide gel, thus, provides an ideal suspending medium for the separation or analysis of macromolecules.

In another aspect of the present invention, a method for preparing a degradable polyacrylamide gel is provided. In one step of the method, an polyacrylamide can be cross-linked with at least one degradable cross-linker. The at least one degradable cross-linker can have the formula (III):

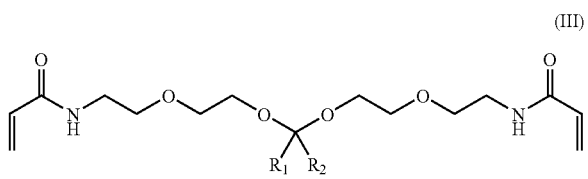

(III)

wherein $R_1$ and $R_2$ may be the same or different. $R_1$ and $R_2$ may comprise hydrogen, an alkyl, or a substituted alkyl.

In general, the degradable polyacrylamide gel is formed by the co-polymerization of acrylamide monomers and the at least one cross-linker in an appropriate buffer having a pH buffering (e.g., capacity between about 3.0 and 11.0). Examples of buffers that can be used include tris-borate-EDTA (TBE), trishydroxyaminomethane (TRIS, THAM), ethylamine (EA), diethylamine (DEA), ethanolamine (EOA), (3-[cyclohexylamino]-2-hydroxy-1-propane sulfonic acid (CAPSO), (2-[N-cyclohexylamino]ethane sulfonic acid (CHES), (3-[1,1-dimethyl-2-hydroxy ethyl)amino]-2-hydroxypropanesulfonic acid) (AMPSO), (N,N-bis[2-hydroxyethyl)glycine (BICINE), (3-[N,N-bis(2 hydroxyethyl)amino]-2-hydroxy propane sulfonic acid) (DIPSO), (N-[2-hydroxyethyl]piperazine-$N^1$-[2-ethanesulfonic acid (HEPES), (N,N-bis[2-hydroxyethyl]glycine) (BICINE), triethano-lamine (TEA), (N-tris[hydroxymethyl]methyl glycine (TRICINE), (N-tris [hydroxymethyl]-3-aminopropane sulfonic acid) (TAPS), (N-[2-hydroxyethyl]piperazine-$N^1$-[3-propane sulfonic acid] (EPPS), (N-[2-hydroxyethyl]piperazine-$N^1$-[2-hydroxy propane sulfonic acid] (HEPPSO), and (piperazine-N,$N^1$-bis[hydroxy propane sulfonic acid] (POPSO).

The acrylamide monomers polymerize into long chains which are cross-linked at intervals by the at least one degradable cross-linker, thereby forming the degradable polyacrylamide gel. The porosity of the degradable polyacrylamide gel can be altered by changing the percentage of acrylamide used and/or the amount of the at least one cross-linker present. For example, a higher percentage of acrylamide will yield a denser gel with better ability to separate smaller macromolecules. In contrast, a lower percentage of acrylamide will yield a more porous gel that generally favors the separation of larger macromolecules.

In an example of the method, a degradable polyacrylamide gel may be prepared by dissolving about 0.95 g of acrylamide and about 0.05 g of the at least one degradable cross-linker in about 2.5 mL of TBE buffer. To prepare a cross-linked gel of about 10% (w/w), about 2.5 mL of the dissolved solution may be mixed with about 7.5 mL of TBE buffer. Next, about 10 mg of ammonium persulfate may be added and mixed well for about 5 minutes. About 4 μL of TEMED may be added to the mixture, which may then be incubated at about room temperature for about 2 hours.

Figure 2:
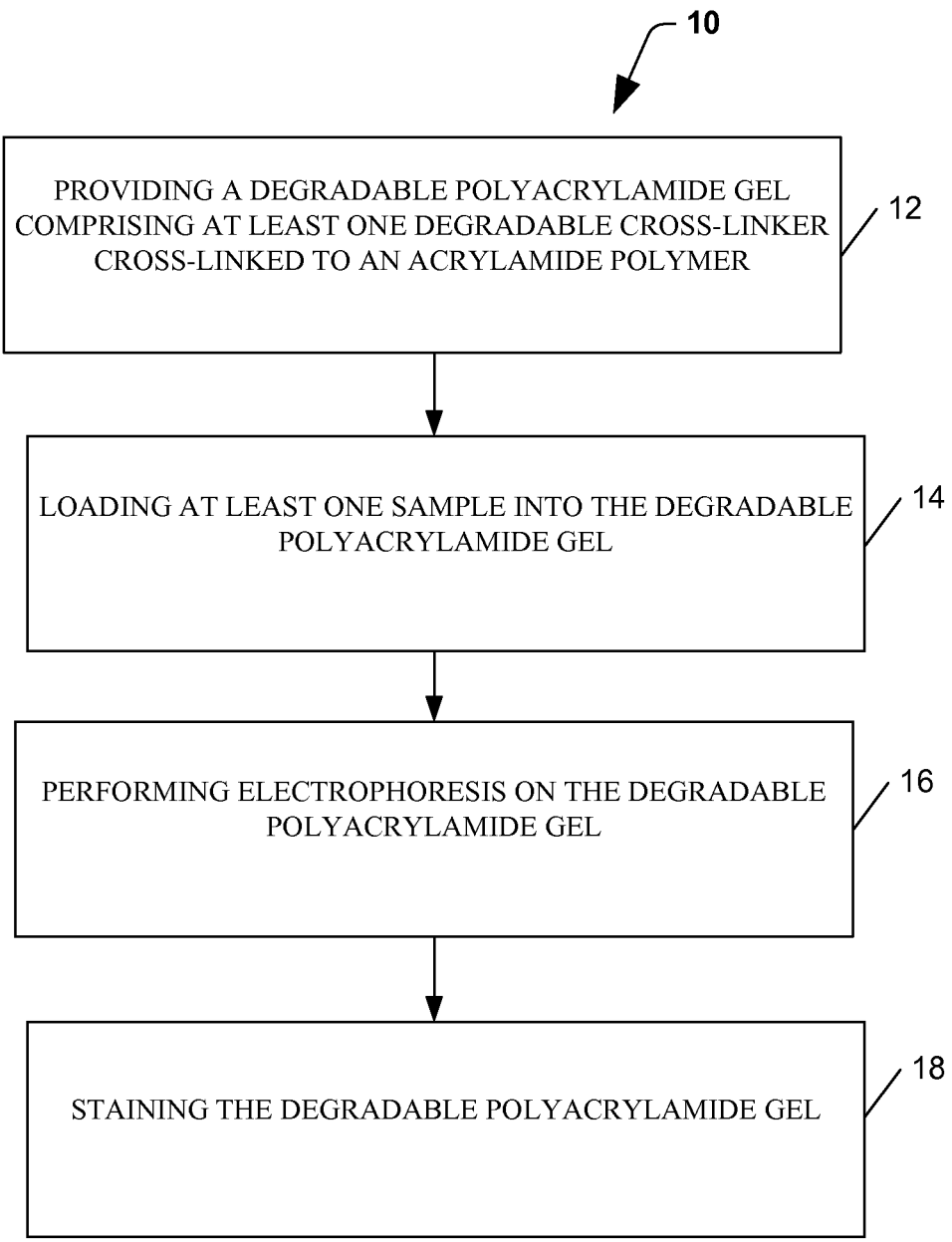
FIG. 2 is a flow diagram illustrating a method for separating or analyzing at least one macromolecule in a sample.

FIG. 2 is a flow diagram illustrating another aspect of the present invention. In FIG. 2, a method 10 of separating or analyzing at least one macromolecule in a sample is provided. In general, the methods of the present invention can be used with a wide range of sample types. Essentially any macromolecule-containing sample can be utilized with the methods described herein. The samples can contain a relatively small number of macromolecules or can contain a large number of macromolecules, such as all the proteins expressed within a cell or tissue sample, for example.

Samples can be obtained from any organism or can be mixtures of synthetically prepared macromolecules or combinations thereof. Thus, suitable samples can be obtained, for example, from microorganisms (e.g., viruses, bacteria and fungi), animals (e.g., cows, pigs, horses, sheep, dogs and cats), hominoids (e.g., humans, chimpanzees, and monkeys) and plants. The samples can come from tissues, tissue homogenates, or fluids of an organism or cell cultures. Thus, for example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components.

Sample preparation for various electrophoresis techniques is known in the art. If a sample contains cellular debris or other non-protein material that might interfere with separation during electrophoresis, for example, such material can be removed using any of a variety of known separation techniques, including forcibly exuding the sample through sieve material, filtration and centrifugation. Samples whose ionic strength is particularly high can be desalted using established techniques such as dialysis, dilution, and re-concentration, for example.

In general, the method 10 comprises the use of electrophoresis to separate or analyze the at least one macromolecule. Gel electrophoresis generally comprises three main steps, the first of which includes preparing a polyacrylamide gel. At 12, a degradable polyacrylamide gel may be prepared as described above. For example, an acrylamide polymer and at least one degradable cross-linker may be cross-linked in an appropriate buffer solution. The at least one degradable cross-linker may include a ketal or acetal group having the formula (I):

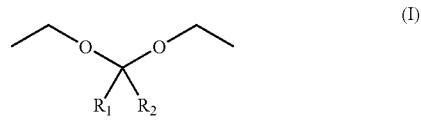

wherein $R_1$ and $R_2$ are the same or different and are hydrogen, an alkyl, or a substituted alkyl.

Alternatively or additionally, the at least one degradable cross-linker may comprise a ketal or acetal group having the formula (II):

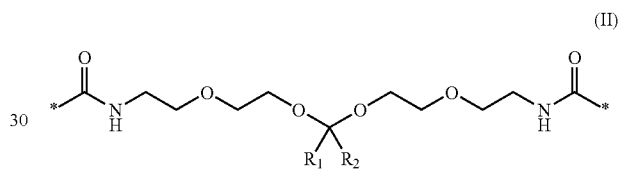

wherein $R_1$ and $R_2$ are the same or different and are hydrogen, an alkyl, or a substituted alkyl.

Polymerization and cross-linking of the acrylamide and the at least one degradable cross-linker can be initiated providing a catalyst (e.g., TEMED) and an initiator (e.g., ammonium persulfate) in a solution containing the acrylamide and cross-linker. The solution can then be quickly transferred to an electrophoresis chamber where polymerization takes place. The polymerization transforms the solution into a firm gel, typically within about an hour. A slot-forming gel comb may then be set in place at one end of the gel.

After polymerizing the degradable polyacrylamide gel, the chamber may be placed in an electrophoresis cell (i.e., where electrophoresis may be performed). In continuous electrophoresis, buffer solution of identical ionic strength, composition and pH as the buffer solution incorporated into the gel during polymerization may be added to each buffer reservoir. In discontinuous electrophoresis, a different buffer solution (but generally having a counter ion common with the buffer polymerized in the gel) may be added to one of the reservoirs. Electrodes in each reservoir may be connected to a direct current power supply.

At this point a complete electric circuit exists and the degradable polyacrylamide gel is ready for application of the at least one sample. At 14, the at least one sample may be loaded into the degradable polyacrylamide gel using, for example, a pipette or other similar device. It will be appreciated that the at least one sample may comprise any number of components needed to properly perform electrophoresis. Such additional components are known in the art and can include, for example, different running buffers, dyes, markers (e.g., protein or DNA size markers), and the like. It should be appreciated that prior to loading the at least one sample, it may be desirable to apply potential to the circuit by means of the power supply. This may be done to cause migration of residual ammonium persulfate and other charged residues of the gel formation process away from the sample application region of the degradable polyacrylamide gel.

After the at least one sample has been loaded into the degradable polyacrylamide gel, electrophoresis may be performed at 16. An appropriate voltage and current may be established by means of the direct current power supply for a time sufficient to complete the resolution of the at least one sample. At 18, several known techniques may then be used to resolve or identify the presence of the at least one sample. Such techniques generally include staining with zinc or copper, Coomassie blue, silver, fluorescent stains (e.g., SYPRO ruby), and the like.

In an example of the method 10, a degradable polyacrylamide gel may be used to analyze or separate a macromolecule, such as a polypeptide, using electrophoresis. About 10 µL of a protein loading buffer and about 10 µL of about 30% of a particular polypeptide may be combined to form samples. The samples may then be loaded into at least one well of the degradable polyacrylamide gel. Electrophoresis may be run at about 4° C. in 150 V for about 60 minutes. After electrophoresis, the degradable polyacrylamide gel may be separated from the electrophoresis apparatus and washed two or more times with de-ionized water. The degradable polyacrylamide gel may then be stained for about 30 minutes at 4° C. with Coomassie blue solution after adjustment to a pH of about 5.0. The degradable polyacrylamide gel may then be destained with de-ionized water for about one hour at about 4° C. with mild shaking.

Figure 3:
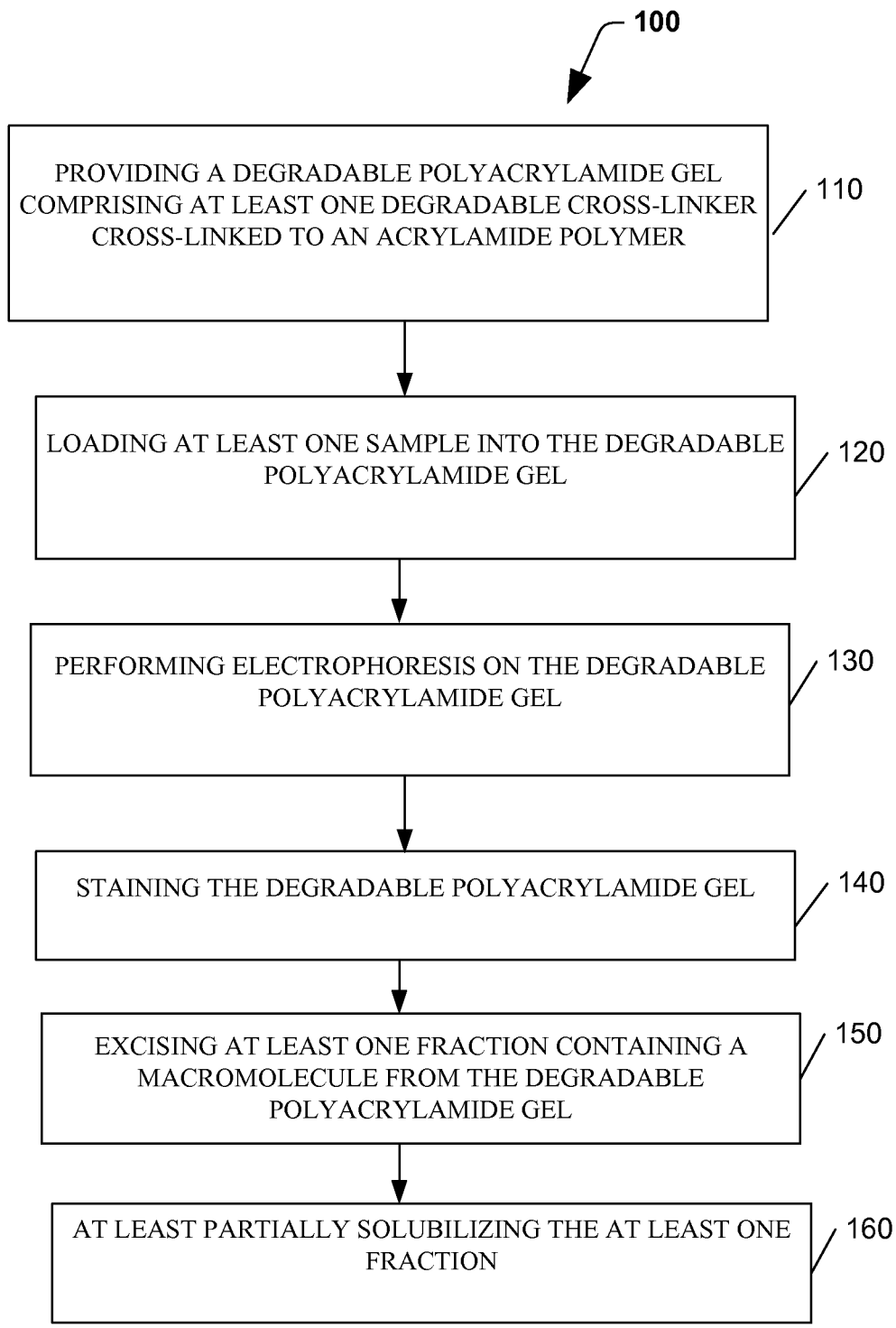
FIG. 3 is a flow diagram illustrating another method for separating or analyzing at least one macromolecule in a sample.
Figure 4:
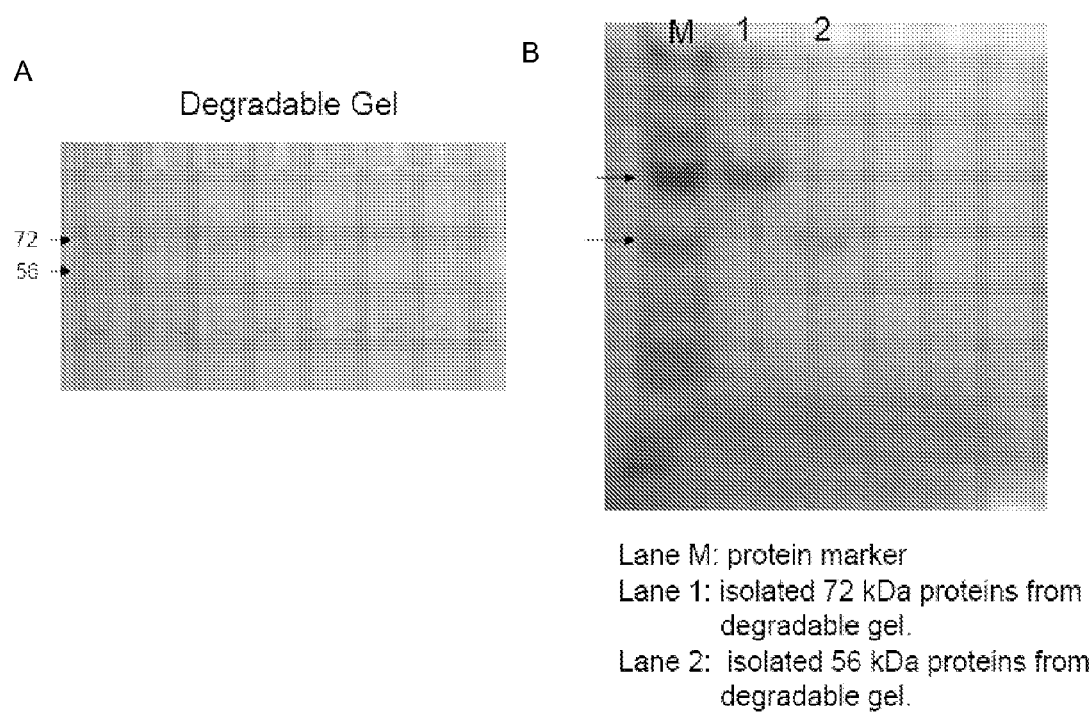
FIGS. 4A-B are SDS-PAGE gels showing the purification of marker proteins using a a degradable polyacrylamide gel of the present invention (FIG. 4A) and confirmation of purified intact proteins using a polyacrylamide gel of the prior art (FIG. 4B)

FIG. 3 is a flow diagram illustrating another aspect of the present invention. In FIG. 3, a method 100 is provided for separating or analyzing at least one macromolecule in a sample. In the method 100, a degradable polyacrylamide gel may be prepared at 110 as described above. At 120, at least one sample may then be loaded into the degradable polyacrylamide gel and electrophoresis performed at 130 (as described above). As also described above, the degradable polyacrylamide gel may be stained at 140.

After electrophoresis, a fraction or band of interest may be excised from the degradable polyacrylamide gel at 150. The fraction of interest may comprise the at least one macromolecule, and may be determined by comparing the position of the fraction on the gel with the position of a particular control marker (also on the gel). Techniques for excising fractions from polyacrylamide gels are known in the art. For example, a fraction of interest may be excised from a gel using a razor blade or other similar tool. The fraction of interest may be carefully excised such that the amount of any excess polyacrylamide removed is minimized.

After excising the fraction of interest, the fraction may be at least partially solubilized at 160 with a solubilizing agent. The solubilizing agent can include any agent that facilitates hydrolysis of the ketal or acetal group of the at least one degradable cross-linker. For instance, a mild organic acid, such as acetic acid, may be used to hydrolyze or degrade the fraction. As shown in FIG. 1B, addition of the solubilizing agent hydrolyzes the ketal or acetal group of the at least one cross-linker and thereby allows release of a structurally intact macromolecule from the degradable polyacrylamide gel.

In one example of the method 100, a fraction or band of interest may be cut from a degradable polyacrylamide gel after electrophoresis. The extracted band may be placed in a 15 mL centrifuge tube. About 4 mL of acetic acid buffer (about 300 mM acetic acid in de-ionized water) having a pH of about 5.0 may then be added into the centrifuge tube. The centrifuge tube may then be incubated at about 37° C. for about 5 hours with shaking. After incubation, about 0.4 mL of acetonitrile may be added to the centrifuge tube. The centrifuge tube may then be incubated for about 10 minutes at room temperature with occasional shaking. After incubation, about 3.6 mL of acetonitrile may be added to the mixture and vigorously shaken, followed by incubation at about room temperature for about one hour. Next, the precipitated pellet may be removed after centrifugation at about 4200 rpm for about 15 minutes. After centrifugation, the supernatant may be removed from the centrifuge tube and transferred into a 50 mL centrifuge tube. About 10 mL of acetonitrile may then be added to the 50 mL centrifuge tube. The 50 mL centrifuge tube may be shaken and incubated at about room temperature for about 1 hour. The 50 mL tube may then be centrifuged at about 4200 rpm for about 15 minutes. After centrifugation, the resultant pellet, which contains at least one macromolecule, may be re-suspended in about 10 µL of TBE buffer and analyzed as desired.

Degradable polyacrylamide gels of the present invention may find use in any number of known electrophoresis assays. For example, degradable polyacrylamide gels can be used for high throughput electrophoresis. The ease of preparation, predictability, stability, and good resolution make the gels of the present invention ideal for high throughput protein or nucleic acid electrophoresis.

Alternatively, a degradable polyacrylamide gel of the present invention may be used to carry out two-dimensional gel electrophoresis. Two-dimensional gel electrophoresis separates proteins in two steps, based on two independent properties: (1) the first-dimension is isoelectric focusing, which separates proteins according to their isoelectric points (pI); and (2) the second-dimension is SDS-PAGE, which separates proteins according to their molecular weights. The procedure generally involves placing a sample in the gel with a pH gradient and then applying a potential difference across it. In the electrical field, the protein can migrate along the pH gradient until it carries no overall charge. This location of the protein constitutes the apparent pI of the protein. The second step is performed in slab SDS-PAGE.

Because the methods of the present invention can provide structurally intact macromolecules, it should be appreciated that resolved macromolecules, i.e., proteins, can be further analyzed by non-electrophoretic methods. Examples of such methods include infrared spectroscopy, nuclear magnetic resonance spectroscopy, UV/VIS spectroscopy, and complete or partial sequencing. Coupling the current electrophoretic-based methods to various mass spectroscopy (MS) methods is one specific example of further analysis that can be conducted. A variety of mass spectral techniques can be utilized including, for example, several MS/MS methods and electrospray-time of flight MS methods. Such methods can be used to determine at least a partial sequence for proteins resolved by the electrophoretic methods.

Figure 7:
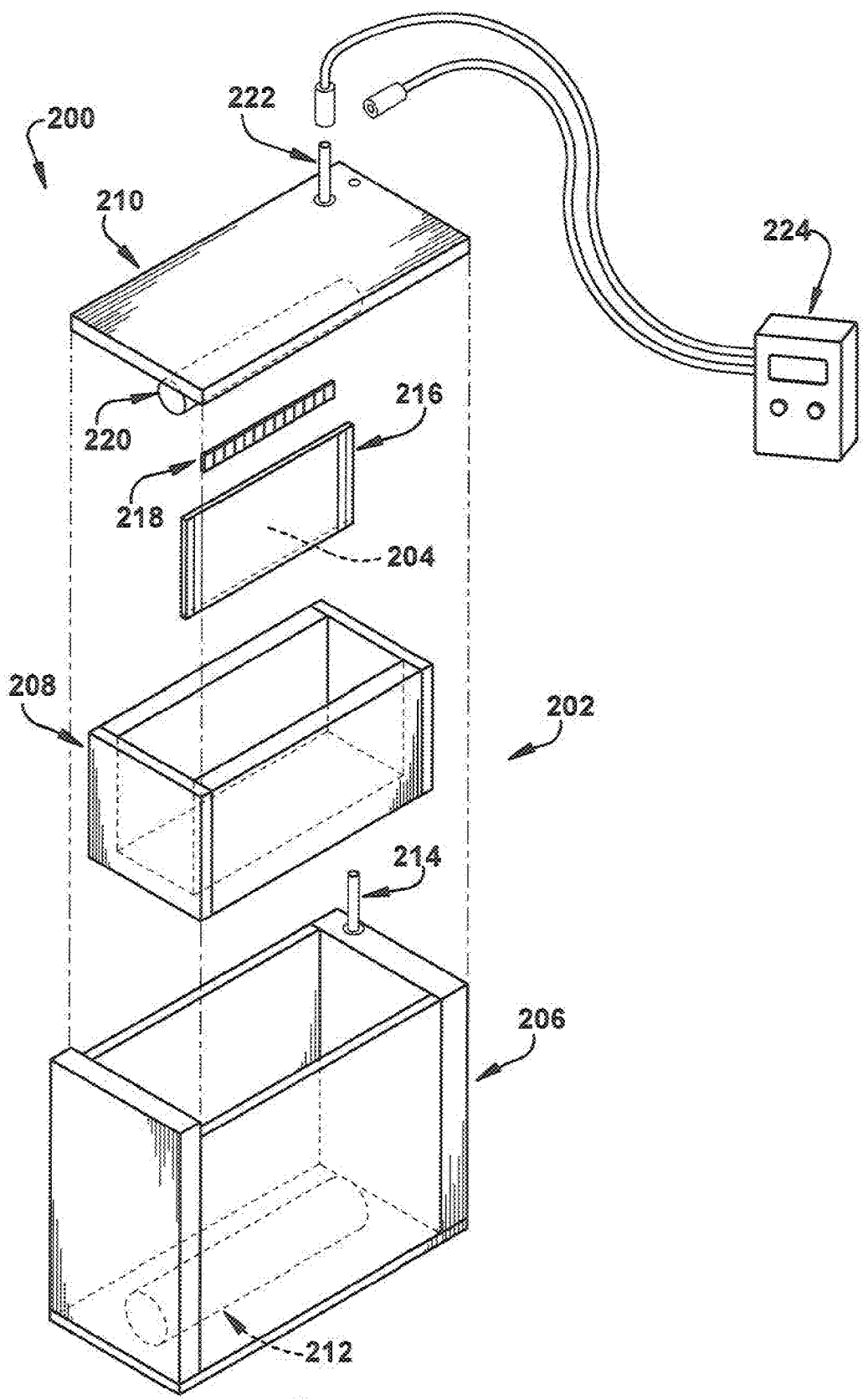
FIG. 7 is a perspective view of an electrophoresis apparatus for separating or analyzing at least one macromolecule in a sample constructed in accordance with the present invention.

FIG. 7 illustrates another aspect of the present invention. FIG. 7 shows an electrophoresis apparatus 200 for separating or analyzing at least one macromolecule in a sample. The electrophoresis apparatus 200 may comprise an electrophoretic cell 202 and a degradable polyacrylamide gel 204 disposed in the cell. The electrophoretic cell 202 may comprise a tank 206, an upper tank 208, and a cover set 210. The tank 206 is capable of receiving the upper tank 208. The tank 206 can include a first electrode 212 (i.e., and anode) and a first electrode jack 214. The tank 206 may be comprised of any suitable plastic or hard plastic polymer.

The upper tank 208 may be slidably received in the tank 206. The upper tank 208 can include a track (not shown) for receiving a cassette 216. The cassette 216 provides a housing for the degradable polyacrylamide gel 204. The cassette 216 may be comprised of any suitable plastic or hard plastic polymer. As shown in FIG. 7, a comb 218 or other similar device may be inserted into the cassette 216. The comb 218 serves to form "lanes" in which samples may be loaded into the degradable polyacrylamide gel 204.

The cover set 210 can include a second electrode 220 (i.e., a cathode) and a second electrode jack 222. The first and second electrode jacks 214 and 222 may be operably coupled to a power source 224 capable of generating an electric current. The cover set 210 may be placed atop the tank 206 and the power source 224 connected to the second electrode jack 222. When the apparatus 200 is properly assembled, a complete electrical circuit may be formed.

As described above, the degradable polyacrylamide gel 204 can include a polyacrylamide cross-linked with at least one degradable cross-linker including a ketal or acetal group having the formula (I):

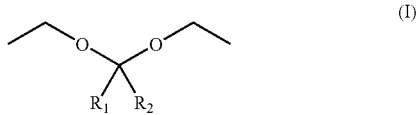
(I)

wherein $R_1$ and $R_2$ are the same or different and are hydrogen, an alkyl, or a substituted alkyl. Alternatively or additionally, the at least one degradable cross-linker can include a ketal or acetal group having the formula (II):

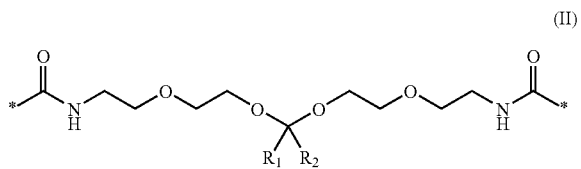
(II)

wherein $R_1$ and $R_2$ are the same or different and are hydrogen, an alkyl, or a substituted alkyl.

The apparatus 200 may be used to separate or analyze at least one macromolecule in a sample using any known electrophoretic technique including, but not limited to, SDS-PAGE, one- and multi-dimensional gel electrophoresis, Western blots, spectroscopy, and the like. It will be appreciated that the electrophoresis apparatus 200 illustrated in FIG. 7 and described herein is intended to be illustrative and, moreover, that degradable polyacrylamide gel 204 according to the present invention can be used with any known electrophoresis device.

The following examples are for the purpose of illustration only and are not intended to limit the scope of the claims, which are appended hereto.

EXAMPLE 1

Preparation of Degradable Polyacrylamide Gel 0.95 g of acrylamide (FISHER SCIENTIFIC) and 0.05 g of ketal cross-linker was dissolved in 2.5 mL of TBE (FISHER SCIENTIFIC). 2.5 mL of dissolved solution was mixed with 7.5 mL of TBE buffer to prepare 10% (w/w) cross-linked gel. 10 mg of ammonium persulfate (FISHER SCIENTIFIC) was added and mixed well for 5 minutes. 4 μL of TEMED (FISHER SCIENTIFIC) was added to the mixture. The mixture was incubated at room temperature for 2 hours.

EXAMPLE 2

Electrophoresis Using the Degradable Polyacrylamide Gel

Figure 5:
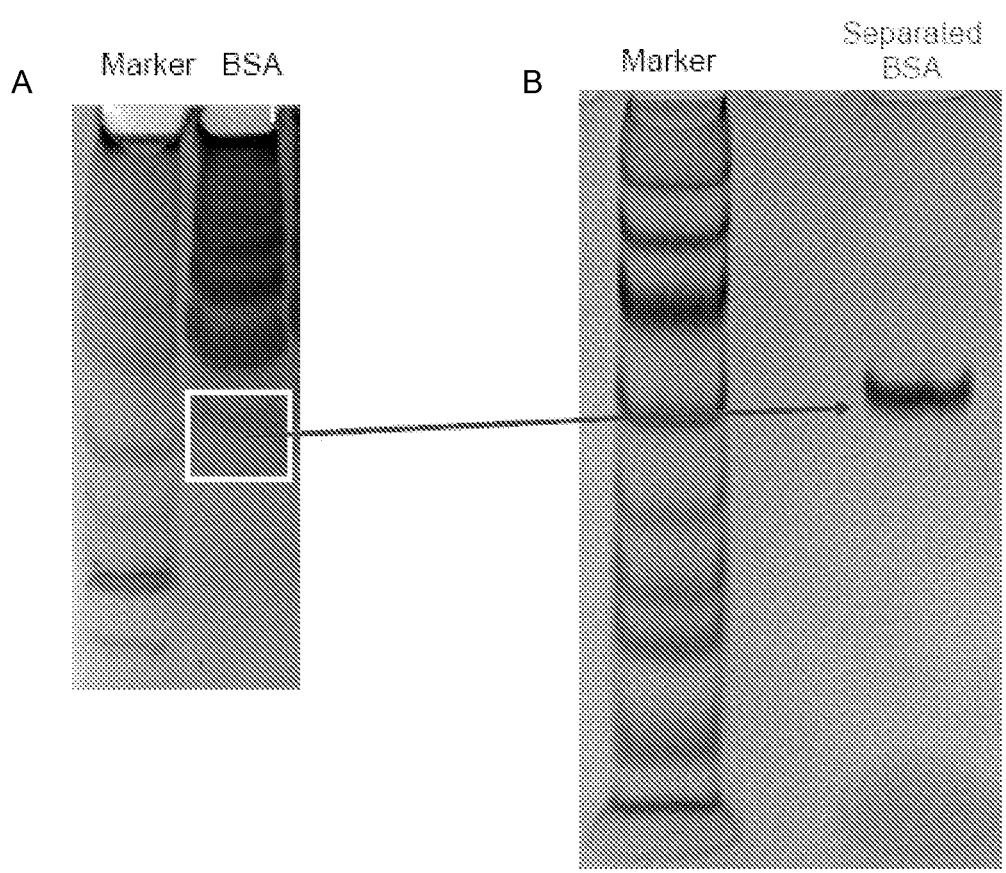
FIGS. 5A-B are SDS-PAGE gels including purified bovine serum albumin (BSA).
Figure 6:
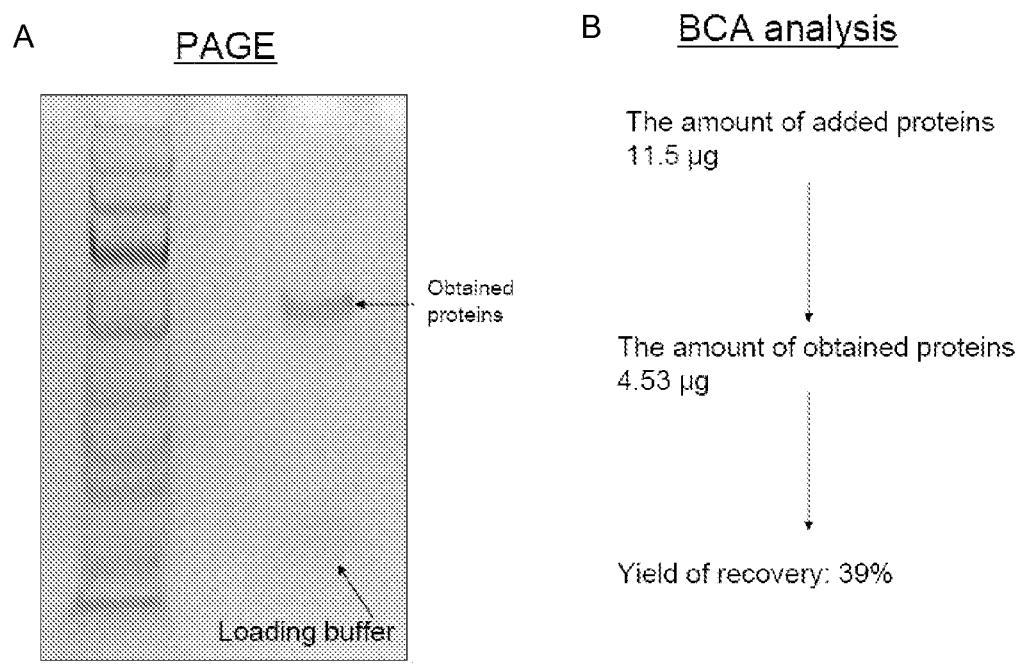
FIGS. 6A-B show the recovery yield of BSA from the degradable polyacrylamide gel of FIG. 5A.

Protein marker and BSA (SIGMA ALDRICH) samples made of 10 μL of 30% BSA and 10 μL of protein loading buffer (FISHER SCIENTIFIC) were loaded in the wells. The electrophoresis was run at 4° C. in 150 V for 60 minutes. The gel was separated from the apparatus and washed twice with de-ionized water. The gel was stained 30 minutes at 4° C. with Coomassie blue solution (FISHER SCIENTIFIC) after adjustment to pH 5.0. The gel was destained with deionized water for 1 hour at 4° C. with mild shaking (FIG. 5A).

EXAMPLE 3

Protein Isolation from the Degradable Polyacrylamide Gel

The band of interest (monomeric protein) was cut. The extracted band gels were placed in 15 mL centrifuge tubes including 4 mL of pH 5 acetic acid buffer (300 mM acetic acid in de-ionized water). The tubes were incubated at 37° C. for 5 hours with shaking for degradation. 0.4 mL of acetonitrile was added to the tubes after degradation (1/10 volume acetonitrile). The tubes were then incubated for 10 minutes at room temperature with occasional shakings. 3.6 mL of acetonitrile was added to the tubes, which were then vigorously shaken followed by incubation at room temperature for 1 hour. The precipitated pellet (precipitated polyacrylamide) was removed after centrifugation at 4200 rpm for 15 minutes. The supernatant obtained was transferred to a 50 mL centrifuge tube and 10 mL of acetonitrile was added (80% acetonitrile). The 50 mL tube was vigorously shaken and incubated at room temperature for 1 hour. The precipitated pellet (precipitated protein) was isolated after centrifugation at 4200 rpm for 15 minutes. The protein pellet was then re-suspended in 10 μL of TBE buffer. The protein was analyzed using a conventional polyacrylamide gel (10% cross-linking) synthesized with acrylamide and methylene bisacrylamide cross-linker (FIG. 5B). The intact structure of the protein was examined, and the intact structure of BSA fraction was confirmed.

EXAMPLE 4

In the following example, we describe a novel approach to extract intact proteins keeping the quaternary structure of proteins using a degradable gel in acidic condition prepared by acetal crosslinker instead of bis-acrylamide. The hydrolysis of acetal crosslinker was depicted FIG. 1. Mouse IgG1 monoclonal antibody of 150 kDa was electrophoresed without any reducing agents including SDS (sodium dodecylsulfate) and the recovered amount of biologically active IgG1 was quantified using an ELISA (enzyme-linked immunosorbent assay) kit after hydrolysis of gel in acidic solution.

Native Gel Electrophoresis

Different concentration of degradable gels (6%, 8%, 10%, and 12%) with 5 wt % acetal crosslinker were prepared and run under 150 V for 80 min after 2.7 μg of IgG1 with glycerol and bromophenol blue dye was loaded in each well. Tris-CAPS buffer (60 mM of Tris and 40 mM of 3-(cyclohexylamino)-1-propanesulfonic acid) of pH 9.6 was used as a running buffer because pI value of antibody IgG1 was close to 8. Any reducing agents, even SDS which can denature proteins, were not used. Gels were stained with acidic/silver nitrate which allowed gel permeation with silver ions at acidic pH, followed by reduction to elemental metallic silver with formaldehyde at alkaline pH. As gel concentration was higher, protein moved downward more slowly and resolution (separation) was better, especially at low MW. In contrast, 6% gel showed poor resolution. For further study, 8% or 10% gel was selected since the resolution was good enough at least at high MW (150 kD of IgG1) even though the best resolution could be obtained when 8~12% gradient gel is run. Except for the top band, which is intact mAb IgG1, the rest of bands were considered as free heavy chain and light chain or partially assembled antibodies. Only top bands could be quantified by ELISA, and sharp middle bands and thick bottom bands did not show any specificity in mouse IgG1 ELISA. In order to optimize the crosslinking ratio, 8% gels with different amount of acetal crosslinker (2.5, 5, and 10 wt % of total monomer amount) were prepared. Use of either 5% or 10% of crosslinker in case of 8% gel showed good resolution.

Quantification of Released IgG1 from Gels Using ELISA

In order to quantify the amount of IgG1 released from hydrolyzed gels, ELISA (enzyme-linked immunosorbent assay) was conducted. Top bands (intact IgG1 of MW ~150 kDa) were carefully excised using a sharp scalpel. Each excised band was incubated in hydrolyzing solution for more than 2 hours at room temperature. After ELISA assay was done, UV absorbance at 450 nm was measured. Gompertz growth model was fitted using Matlab for wider working range and more accurate standard curve fitting. Concentration of IgG1 was calculated from absorbance based on Gompertz model and dilution factor was multiplied. Data points of concentration within the range of 7.8~250 ng/ml were averaged. Data showing too low absorbance was excluded because those could easily make erroneous results due to low sensitivity and also small error can be amplified because of large dilution factor multiplied. For comparison, released IgG1 amount measured by ELISA was divided by the original IgG1 amount loaded in a gel.

1) Investigation on IgG1 Release Using Different Hydrolyzing Solution

After running 8 and 10% gels with 5 wt % acetal crosslinker for 80 min under 150 V, half of a gel was stained with silver nitrate. Both top bands of silver stained and unstained gels were hydrolyzed overnight in 3 ml of three different solutions of pH 3, 5 mM formic acid, 5 mM formic acid with 10 vol % of 2-propanol, and 100 mM acetate buffer with gentle shaking. After three hours, all the gel pieces except for 12% gel were completely dissolved and liquidified even though silver stained gels were rather slowly hydrolyzed than unstained ones.

Figure 8A:
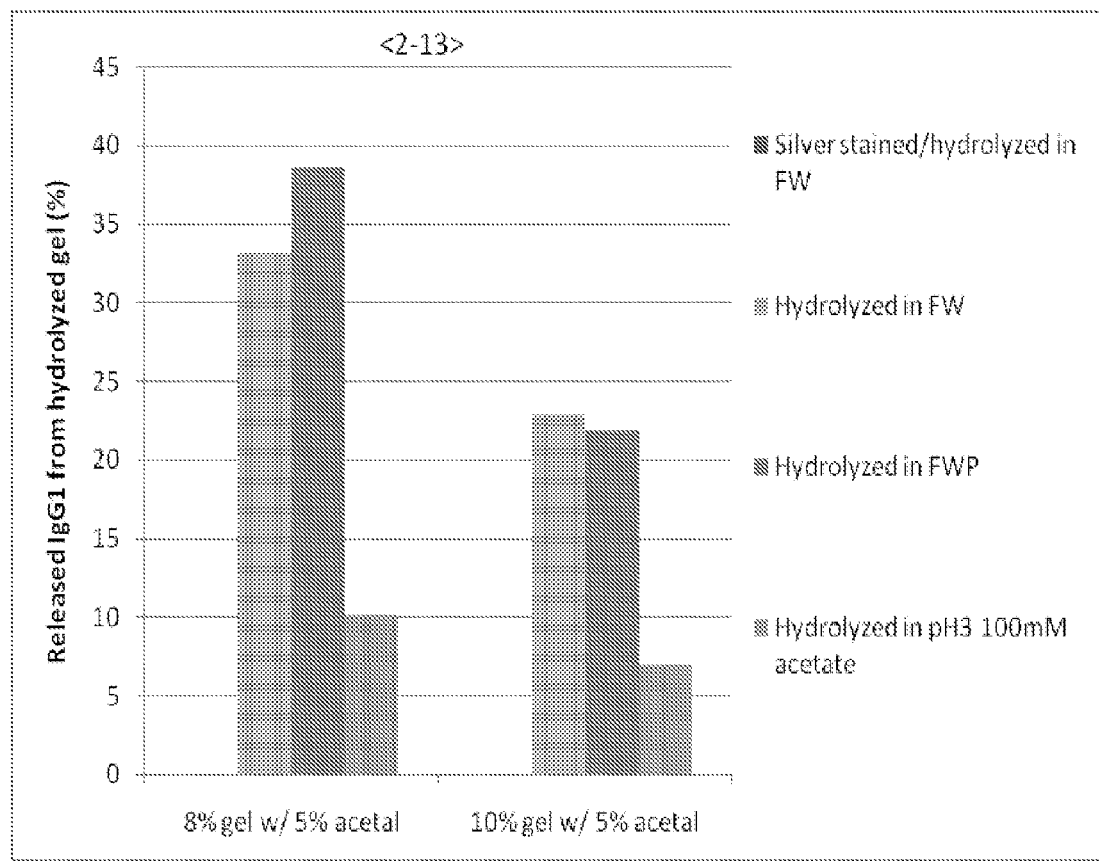
FIG. 8A-C illustrate graphs showing released IgG1 from hydrolyzed gel in different hydrolyzing solution; 5 mM formic acid, 5 mM formic acid with 2-propanol (10 vol %) and 100 mM acetate buffer, was quantified using ELISA.
Figure 8B:
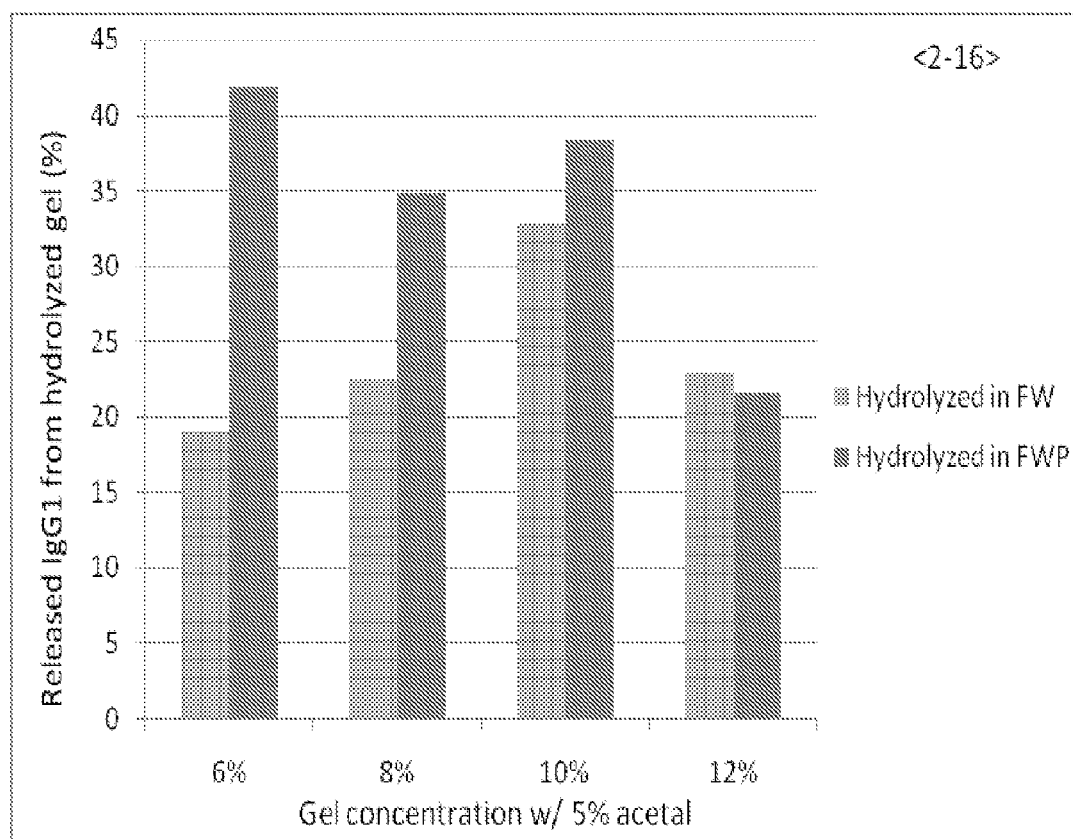
Figure 8C:
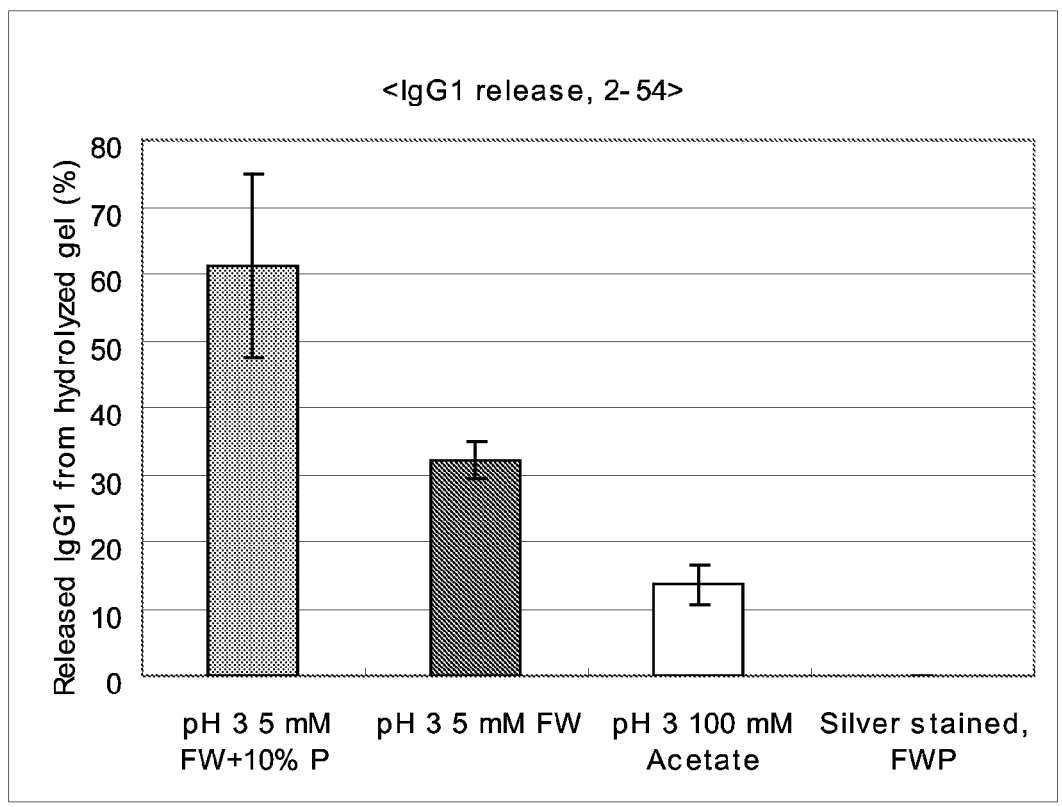

Referring to FIG. 8, silver stained gel piece did not show any active antibody release. It was supposed that formaldehyde used as a developing reagent in the process of silver staining affected on IgG1 activity, so that there was no color development in ELISA. Hydrolysis with FWP (90 vol % of 5 mM formic acid of pH 3 with 10 vol % of 2-propanol) and FW (5 mM formic acid of pH 3) released up to 61% and 32% of IgG1, respectively, from 10% gel with 5% acetal crosslinker. Addition of 10% 2-propanol helped more release of IgG1. Formic acid with 2-propanol has been used as a RP-HPLC (reversed-phase high performance liquid chromatography) eluent since this combination had excellent protein-solubilizing properties, especially for large hydrophobic protein. IgG1 release was only 13% when hydrolyzed in 100 mM pH 3 acetate buffer. Probably smaller formate was more effective to extract protonated IgG1 at pH 3 than acetate. Optimal extraction efficiency was obtained with the formic acid/2-propanol (FWP) combination.

Figure 9A:
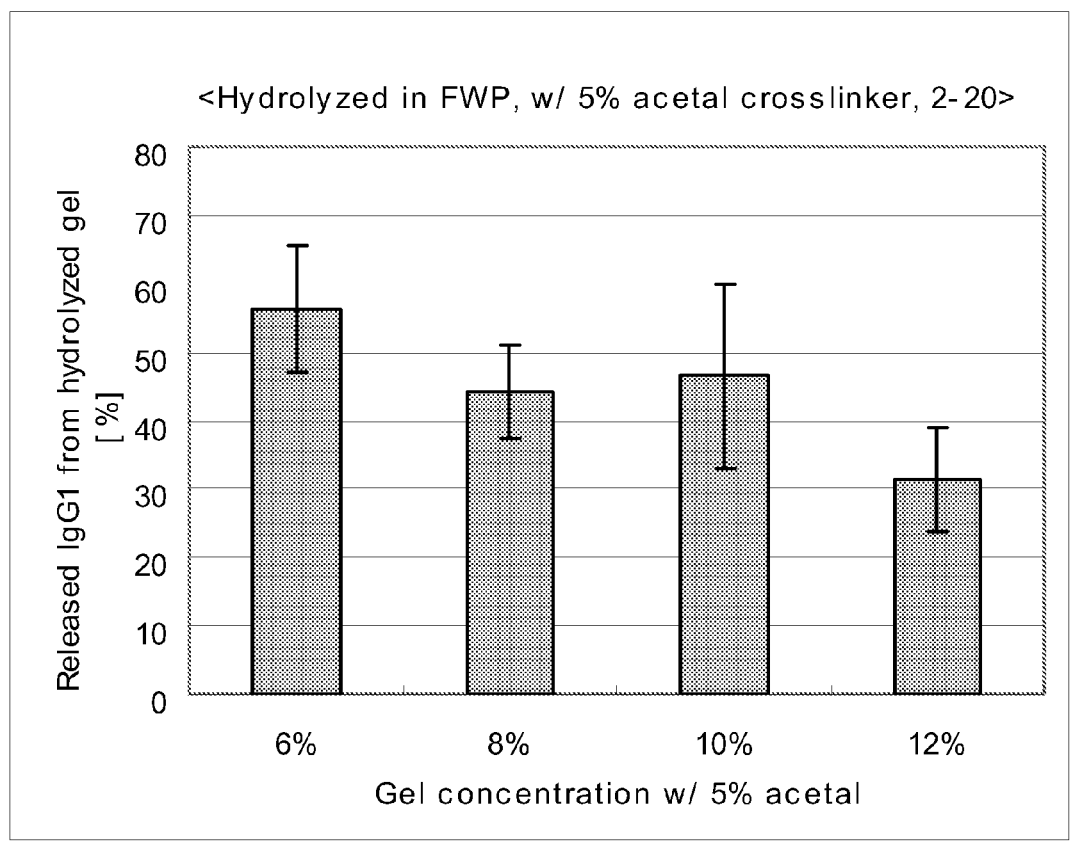
FIG. 9A-B illustrate graphs showing that release of IgG1 was compared after hydrolysis of gels in FWP, 6, 8, 10, and 12% gels with 5 wt % of acetal crosslinker, and 8% gels with 2.5, 5, and % gels with 2.5, 5, and 10 wt % of crosslinker.
Figure 9B:
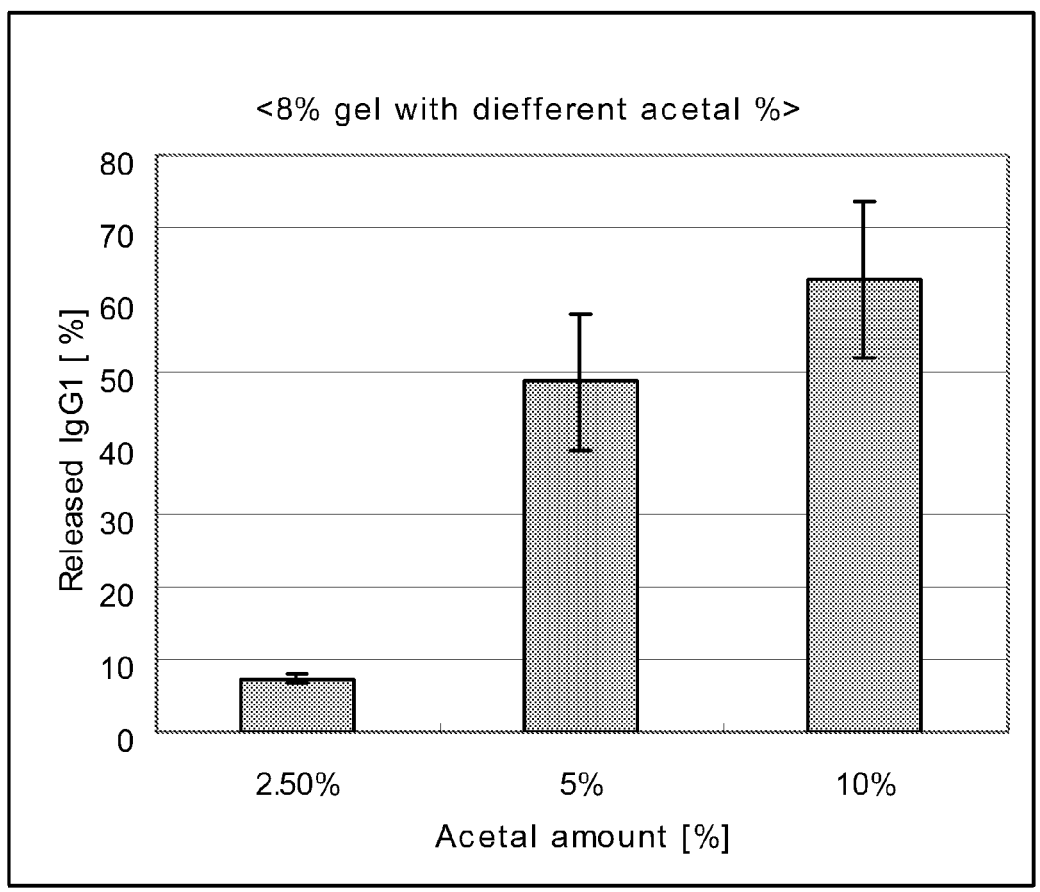

2) Investigation on IgG1 Release Depending on Gel Concentration and Crosslinker Amount Referring to FIG. 9, 6% gel showed the largest amount of release of IgG1, around 56%, and 12% gel showed the least, 32%, supposing that either only partial hydrolysis or high polymer concentration made very little space so that large IgG1 hardly came out from the polymer network. 8% gel with 2.5% crosslinker released IgG1 less than 10% and it could be explained that most of protein was diffused out through relatively big pore of polymer network while handling the gel (running, immersing in Tris/CAPS buffer during staining).

3) Comparison of IgG1 Release from Degradable Acetal and Nondegradable Bis-AA Gel At first, both polyacrylamide gels with acid-degradable acetal crosslinker and nondegradable typical bis-acrylamide were prepared with 8% of total gel concentration and 5 wt % of crosslinker. For better comparison, the same molar % of crosslinker should have been used rather than the same wt % even though the reactivity in polymerization of each crosslinker might be different. From the simple calculation, the same molar amount of acetal crosslinker with 2.67 wt % bis-acrylamide (commercialized) was 6 wt % of total monomer weight.

After incubation at room temperature for 30 min. 8% gel with 5% acetal was completely liquidified, in contrast, a gel piece made with bis-AA remained as it was.

Figure 10:
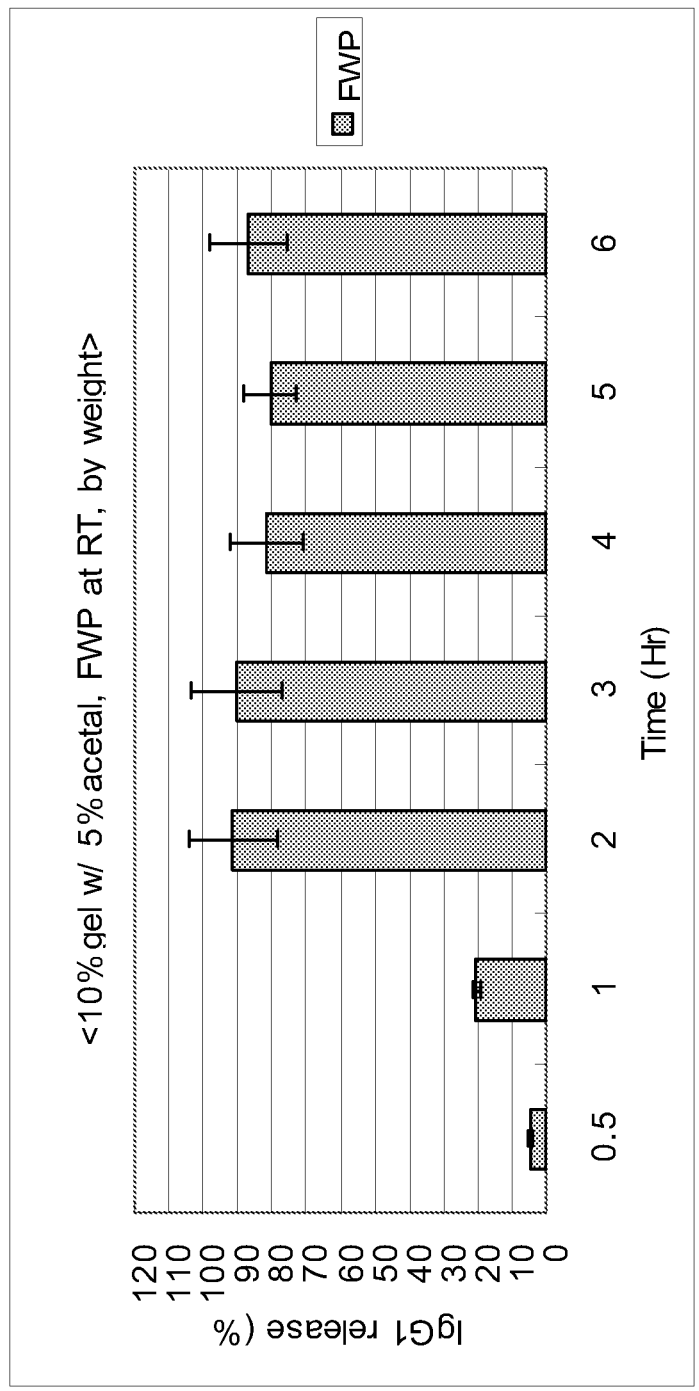
FIG. 10 illustrates graphs of an IgG1 release profile by time from 10% gel with 5 wt % acetal.

In order to find out the time point showing the maximum release of IgG1 when hydrolyzed in FWP solution, 10% gel with 5 wt % acetal was prepared and 600 μl of solution was taken at each hour after hydrolysis solution was added. Referring to FIG. 10, the maximum amount of IgG1 was released 2-3 hr after adding FWP solution.

To investigate how much IgG1 was released in water or Tris-CAPS buffer by simple diffusion and compare with release via hydrolysis using FWP for extended time up to 24 hr, the same experiment was done as above except 600 μl of sample was taken at 1, 2, 3, 6, 12, 24 hr time point after adding each solution and sample was incubated at 4° C. for 24 hr to prevent loss of IgG1 activity or degradation from storing in pH 3 solution at R.T. for a long time.

Figure 11A:
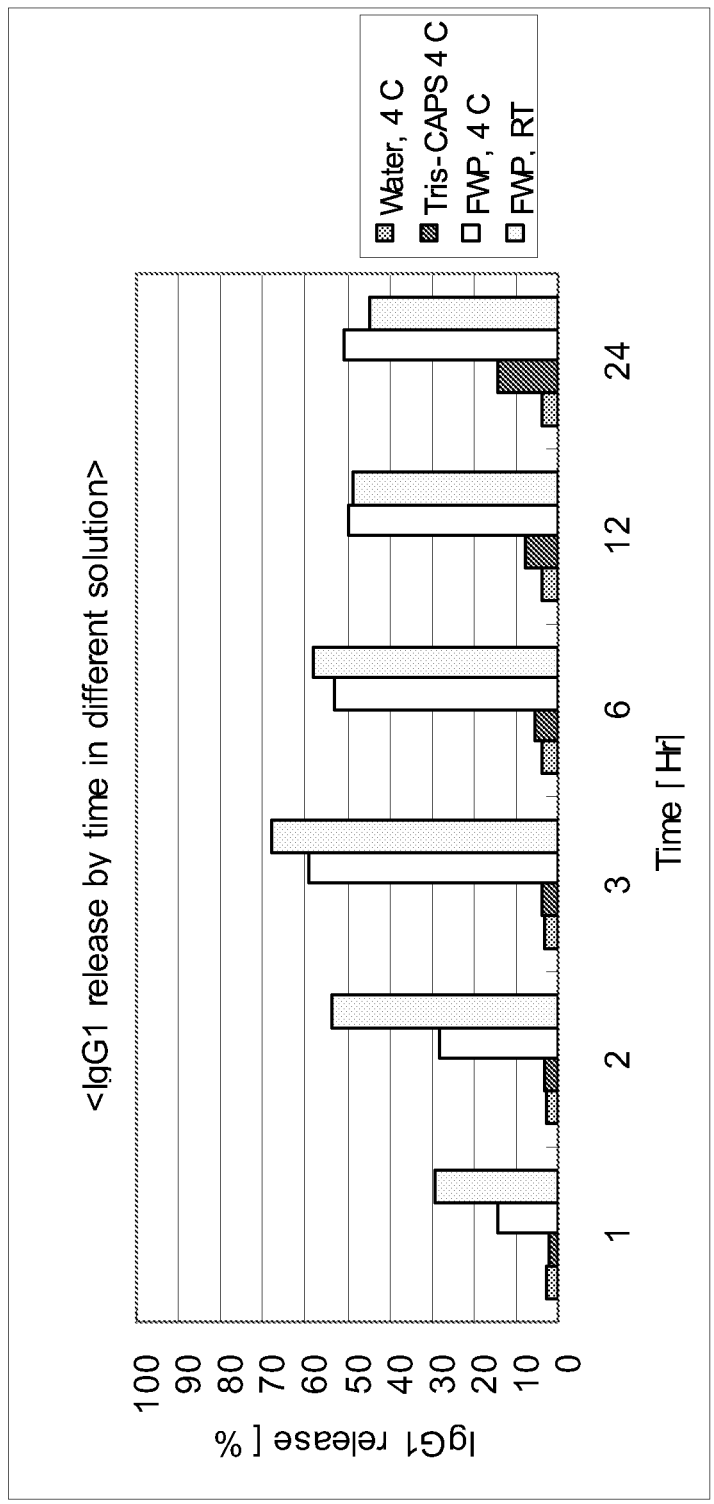
FIG. 11A-B illustrate graphs comparing an IgG1 release profile by time up to 24 hr in water and Tris-CAPS buffer by diffusion and in FWP via hydrolysis.
Figure 11B:
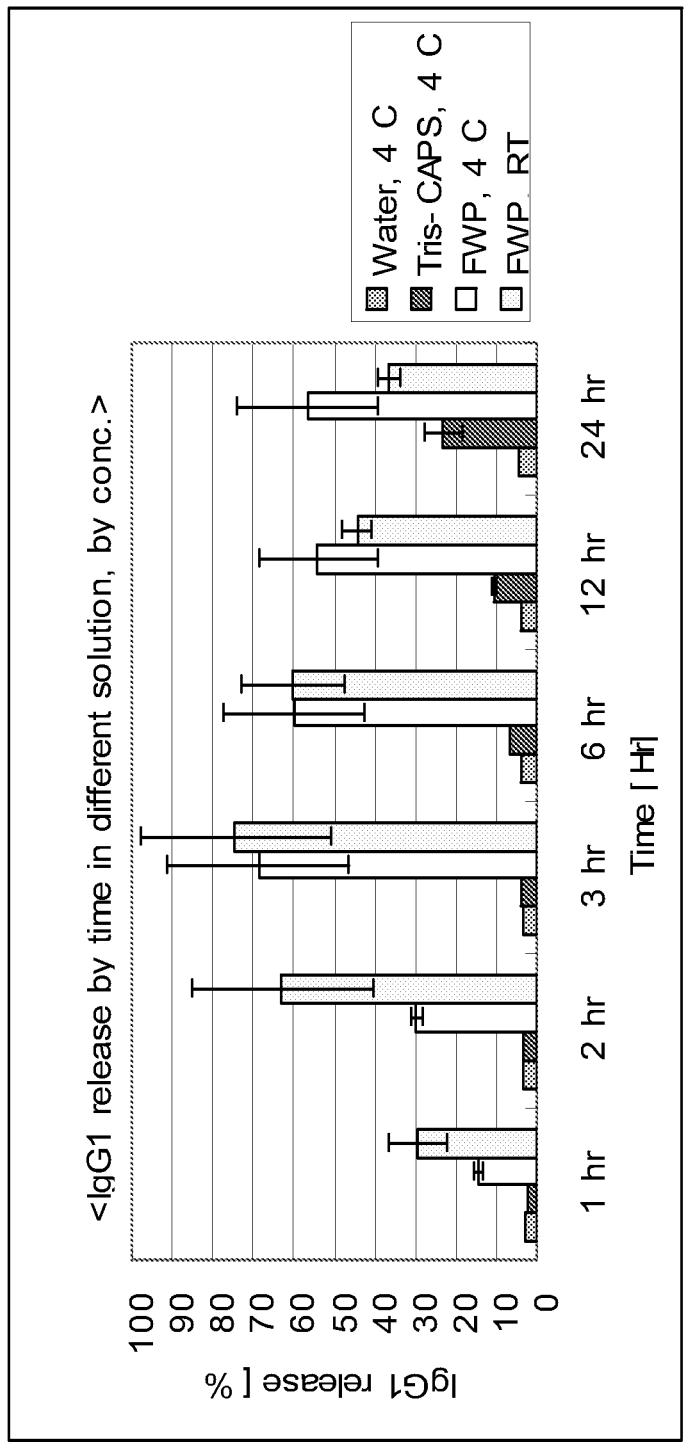

Referring to FIG. 11, protein was not diffused out much when incubated in water and Tris-CAPS, at most 23% after 24 hr incubation in Tris-CAPS buffer. In contrast, IgG1 was released up to 74% when hydrolyzed in FWP for 3 hours.

Conclusion

Novel technology to obtain rather large intact proteins from polyacrylamide gel using acid degradable acetal crosslinker was described. Activity of antibody IgG1 was preserved while running and hydrolyzing a gel in pH 3 solution, and the amount of released IgG1 from a gel was quantified by ELISA. This technology can be extended to 2-D gel electrophoresis and applied to more complicated biological system in order to retrieve functionally active "intact" proteins.

From the above description of the invention, those skilled in the art will perceive improvements, changes and modifications. For example, it should be appreciated that the degradable polyacrylamide gel of the present invention can also be used in place of gels traditionally used in Western blotting. Such improvements, changes and modifications within the skill of the art are intended to be covered by the appended claims.

Having described the invention, the following is claimed:

1. A degradable polyacrylamide gel for analyzing or separating at least one macromolecule in a sample using electrophoresis, the degradable polyacrylamide gel comprising:
at least one degradable cross-linker including a ketal or acetal group having the formula (I):

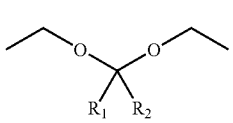

(I)

wherein $R_1$ and $R_2$ are the same or different and are hydrogen, an alkyl, or a substituted alkyl; and an acrylamide polymer cross-linked with the at least one degradable cross-linker, the cross-linker being hydrolysable with an acid having a pH of 3 to 5 after electrophoresis of the sample to release the macromolecule structurally intact.

2. The degradable polyacrylamide gel of claim 1, the at least one degradable cross-linker comprising the formula (II):

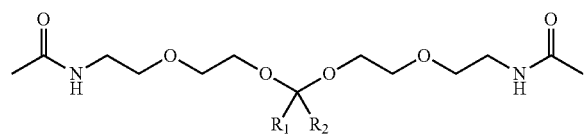

(II)

wherein $R_1$ and $R_2$ are the same or different and are hydrogen, an alkyl, or a substituted alkyl.

3. The degradable polyacrylamide gel of claim 2, the substituted alkyl being $C_1$-$C_5$ alkyl.

4. A degradable polyacrylamide gel for analyzing or separating at least one macromolecule in a sample using electrophoresis, the degradable polyacrylamide gel comprising:
at least one degradable cross-linker including a ketal or acetal group having the formula (II):

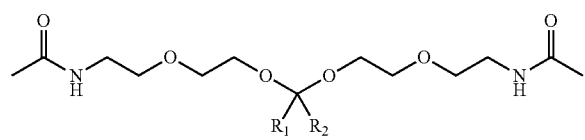

(II)

wherein $R_1$ and $R_2$ are the same or different and are hydrogen, an alkyl, or a substituted alkyl; and an acrylamide polymer cross-linked with the at least one degradable cross-linker, the cross-linker being hydrolysable with an acid having a pH of 3 to 5 after electrophoresis of the sample to release the macromolecule structurally intact.

5. The degradable polyacrylamide gel of claim 4, the substituted alkyl being $C_1$-$C_5$ alkyl.

6. A method of separating or analyzing at least one macromolecule in a sample, the method comprising the steps of:

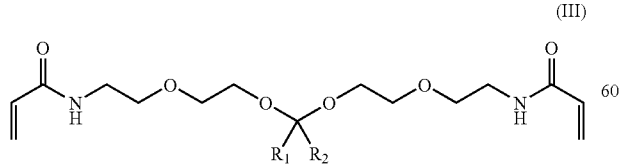

(III)

providing a degradable polyacrylamide gel comprising at least one degradable cross-linker including a ketal or acetal group having the formula (I):

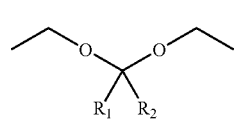

(I)

wherein $R_1$ and $R_2$ are the same or different and are hydrogen, an alkyl, or a substituted alkyl, and an acrylamide polymer cross-linked with the at least one degradable cross-linker;

loading the at least one sample into the degradable polyacrylamide gel;

performing electrophoresis on the degradable polyacrylamide gel; and staining the degradable polyacrylamide gel to visualize the at least macromolecule contained therein, the cross-linker being hydrolyzed with an acid having a pH of 3 to 5 to release the macromolecule structurally intact.

7. The method of claim 6, the at least one degradable cross-linker comprising the formula (II):

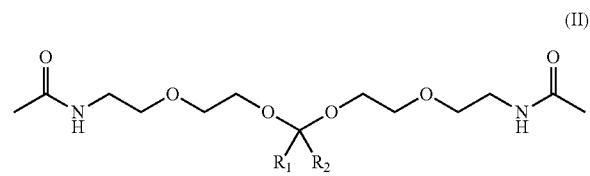

(II)

wherein $R_1$ and $R_2$ are the same or different and are hydrogen, an alkyl, or a substituted alkyl.

8. The method of claims 6, the substituted alkyl being $C_1$-$C_5$ alkyl.

9. The method of claim 6 further comprising the steps of:
excising at least one fraction containing the at least one macromolecule from the degradable polyacrylamide gel; and
at least partially solubilizing the at least one excised fraction.

10. A method of separating or analyzing at least one macromolecule in a sample, the method comprising the steps of:
providing a degradable polyacrylamide gel comprising at least one degradable cross-linker including a ketal or acetal group having the formula (I):

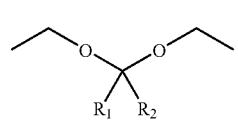

(I)

wherein $R_1$ and $R_2$ are the same or different and are hydrogen, an alkyl, or a substituted alkyl, and an acrylamide polymer cross-linked with the at least one degradable cross-linker;

loading at least one sample into the degradable polyacrylamide gel;

performing electrophoresis on the degradable polyacrylamide gel;

staining the degradable polyacrylamide gel to visualize the at least one macromolecule contained therein;

excising at least one fraction containing the at least one macromolecule from the degradable polyacrylamide gel; and at least partially solubilizing the at least one excised fraction, the cross-linker being hydrolyzed with an acid having a pH of 3 to 5 to release the macromolecule structurally intact.

11. The method of claim 10, the at least one degradable cross-linker comprising the formula (II):

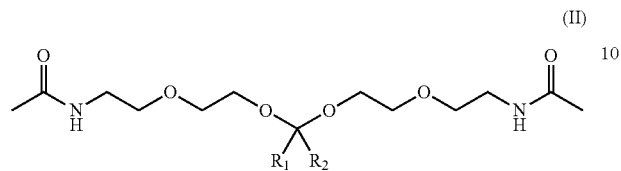

(II)

wherein $R_1$ and $R_2$ are the same or different and are hydrogen, an alkyl, or a substituted alkyl.

12. The method of claim 10, the substituted alkyl being $C_1$-$C_5$ alkyl.

13. An electrophoresis apparatus for separating or analyzing at least one macromolecule in a sample, the electrophoresis apparatus comprising:
an electrophoretic cell; and
a degradable polyacrylamide gel disposed in the electrophoretic cell, the degradable polyacrylamide gel comprising at least one degradable cross-linker including a ketal or acetal group having the formula (I):

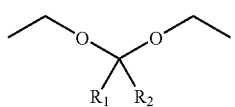

(I)

wherein $R_1$ and $R_2$ are the same or different and are hydrogen, an alkyl, or a substituted alkyl, and an acrylamide polymer cross-linked with the at least one degradable cross-linker, the cross-linker being hydrolysable with an acid having a pH of 3 to 5 after electrophoresis of the sample to release a the macromolecule structurally intact;

wherein the electrophoretic cell comprises a tank, an upper tank, and a cover set for the tank, the upper tank being disposable inside the tank and capable of receiving a cassette in which the degradable polyacrylamide gel is housed, the cover set and the tank each respectively including a cathode and an anode for conducting an electric current therebetween;

wherein the electrophoretic cell is operably coupled to a power source.

14. The apparatus of claim 13, the at least one macromolecule comprising a polynucleotide.

15. The apparatus of claim 13, the at least one macromolecule comprising a polypeptide.

16. The apparatus of claim 13, the at least one degradable cross-linker comprising the formula (II):

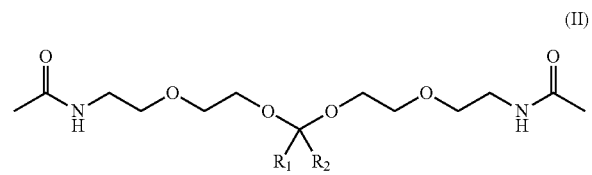

(II)

wherein $R_1$ and $R_2$ are the same or different and are hydrogen, an alkyl, or a substituted alkyl.

17. The apparatus of claim 13, the substituted alkyl being $C_1$-$C_5$ alkyl.

* * * * *